United States Patent [19]
Yale et al.

[11] 3,966,733
[45] June 29, 1976

[54] INTERMEDIATES FOR CERTAIN BENZOTHIADIAZEPINE AND BENZOTHIADIAZOCINE COMPOUNDS

[75] Inventors: Harry Louis Yale, New Brunswick, N.J.; Ramesh B. Petigara, Lansdale, Pa.

[73] Assignee: E. R. Squibb & Sons, Inc., Princeton, N.J.

[22] Filed: Jan. 15, 1975

[21] Appl. No.: 541,165

Related U.S. Application Data
[62] Division of Ser. No. 382,802, July 26, 1973, Pat. No. 3,875,162.

[52] U.S. Cl. ........................................ 260/256.5 R
[51] Int. Cl.² ..................................... C07D 239/04
[58] Field of Search .......................... 260/256.5 R

[56] References Cited
UNITED STATES PATENTS

| | | | |
|---|---|---|---|
| 3,634,427 | 1/1972 | Schweizer et al. | 260/256.5 R |
| 3,704,303 | 11/1972 | Wei | 260/256.5 R |
| 3,740,394 | 6/1973 | Baetz | 260/256.5 R |
| 3,875,162 | 4/1975 | Yale et al. | 260/256.5 R |
| 3,886,160 | 5/1975 | Tweit | 260/256.5 R |

*Primary Examiner*—Leonard Schenkman
*Attorney, Agent, or Firm*—Lawrence S. Levinson; Merle J. Smith; Burton Rodney

[57] ABSTRACT

Compounds of the formula

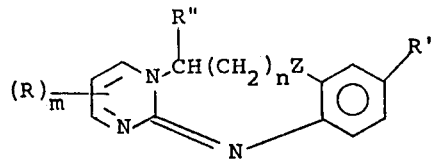

which exhibit central nervous system stimulating properties and act as muscle relaxants, and intermediate compounds therefore, are disclosed.

12 Claims, No Drawings

INTERMEDIATES FOR CERTAIN BENZOTHIADIAZEPINE AND BENZOTHIADIAZOCINE COMPOUNDS

This is a division of application Ser. No. 382,802, filed July 26, 1973, now U.S. Pat. No. 3,875,162.

OBJECTS OF THE INVENTION

It is an object of the present invention to provide new compounds having central nervous system (CNS) stimulating activity. Another object is to provide new compounds having muscle relaxant properties. A further object is to provide intermediates for the preparation of the final compounds of the invention. Yet another object is to provide a method for the preparation of both the intermediate and the final compounds of the present invention. Still another object is to provide a method for the administration of the final compounds of the invention. A still further object is to provide pharmaceutical composition containing as active ingredients the final compounds of the present invention. These and other objects of the present invention will be apparent from the following description.

SUMMARY OF THE INVENTION

The compounds of the present invention have the following formula

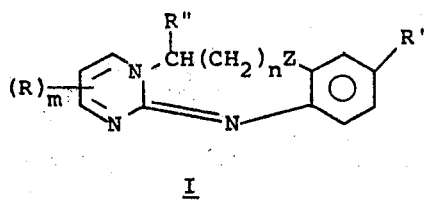

I wherein
- $m$ may be 1 or 2; when $m$ is 1, R occupies either position -4 or -5 of the original 2-aminopyrimidine but when R is halogen it occupies only position-5; when $m$ is 2, the two R's occupy the 4- and 5-positions of the original 2-aminopyrimidine, but only one of the two R-substituents can be halogen and it must occupy the 5-position.
- R may be the same or different and may be hydrogen, halogen (F, Cl, or Br), alkyl of from 1 to 4 carbons, benzyl, phenyl, or mono-substituted phenyl wherein the substituent may be halogen (F, Cl, Br or I), alkyl of from 1 to 4 carbons, alkoxy of from 1 to 4 carbons, or trifluoromethyl;
- R' may be hydrogen, halogen (F, Cl or Br), alkyl of from 1 to 4 carbons, dialkylamidosulfonyl wherein each alkyl radical may have from 1 to 4 carbons, trifluoromethyl;
- $n$ may be 0 or 1;
- R'' may be alkyl of from 1 to 4 carbons, or hydrogen;
- Z may be S or $SO_2$, and pharmaceutically acceptable acid-addition salts thereof.

The foregoing compounds possess central nervous system stimulating properties and act as muscle relaxants.

DETAILED DESCRIPTION

The final compound I of the present invention may be prepared by reacting a 2-aminopyrimidine II wherein R is as previously defined with an o-bromophenyl-Z-alkylene halide III wherein R'' is as previously defined and X is chlorine or bromine. This reaction takes place in any solvent or solvent mixture in which the reactants can be dissolved and which has a boiling point of at least about 100°C. Typical solvents are aromatic hydrocarbons, ethers, aliphatic alcohols or aryl-substituted aliphatic alcohols. Toluene and xylene are examples of suitable aromatic hydrocarbons. Monomethyl ether of diethylene glycol, dimethyl ether of diethylene glycol (diglyme), monomethyl ether of ethylene glycol or dimethyl ether of ethylene glycol (glyme) are examples of suitable ethers. n-Amyl alcohol is an example of a suitable aliphatic alcohol, while benzyl alcohol is an example of a suitable aryl-substituted aliphatic alcohol. Heating compounds II and III in a solvent as described above, or a mixture thereof, at temperatures from about 50° to about 140°C for a period of several hours, typically from about 3 to about 24 hours produces a pyrimidinium compound IV. The latter is converted to an imino compound V by treating with a water miscible alcohol and an alkali metal alkoxide of up to 3 carbon atoms, or with an alkali metal carbonate, e.g., $K_2CO_3$, $Na_2CO_3$, $RbCO_3$, etc. The reaction takes place at room temperature over a period of from about 1 to about 4 hours, or at from about 50° to about 80°C in about 1 hour. Compound V may be converted to the final compound I by treating with a water miscible alcohol and an alkali alkoxide of up to 3 carbons in the presence of copper at a temperature of from about 60° to about 120°C for a period, typically from about 4 to about 10 days. Alternatively, IV may be converted directly to I by heating at a temperature of from about 60° to about 120°C for a period, typically from about 4 to about 10 days, in the presence of potassium carbonate and copper in a solvent such as dimethylformamide, dimethylacetamide, dichlorobenzene, trichlorobenzene, or diethylbenzene. Alternatively, IV may be converted directly to I by heating at a temperature of from about 60° to about 120°C for about 4 to 10 days, typically from about 6 to about 8 days in the presence of an alkali metal hydroxide, alkali metal carbonate, tris-alkali metal phosphate, alkali metal metaborate or alkali metal tetraborate in an anhydrous alcohol solvent, e.g., ethanol, propanol, butanol, pentanol in the presence of copper. Specific examples of suitable compounds include LiOH, NaOH, KOH, RbOH, CsOH, $Na_2CO_3$, $K_2CO_3$, $Rb_2CO_3$, $Cs_2CO_3$, $Na_3PO_4$, $K_3PO_4$, $Rb_3PO_4$, $Cs_3PO_4$, $Na_2B_2O_4$, $Na_2B_4O_7$, $K_2B_2O_4$, and $K_2B_4O_7$.

When m is 1, and when R occupies only the 5-position of II, only one isomer, I, is formed. When $m$ is 1, and when R occupies only the 4-position of IIa, two isomers, Ia and Ib are formed via the intermediates IVa or va and IVb and Vb, respectively. When $m$ is 2, and since the two R's occupy only the 4-, 5-positions, two isomeric products, Ic and Id are formed. The isomers in all instances, can be separated by conventional procedures, e.g., fractional recrystallization or column chromatography.

The foregoing reaction sequence is illustrated by the following equations:

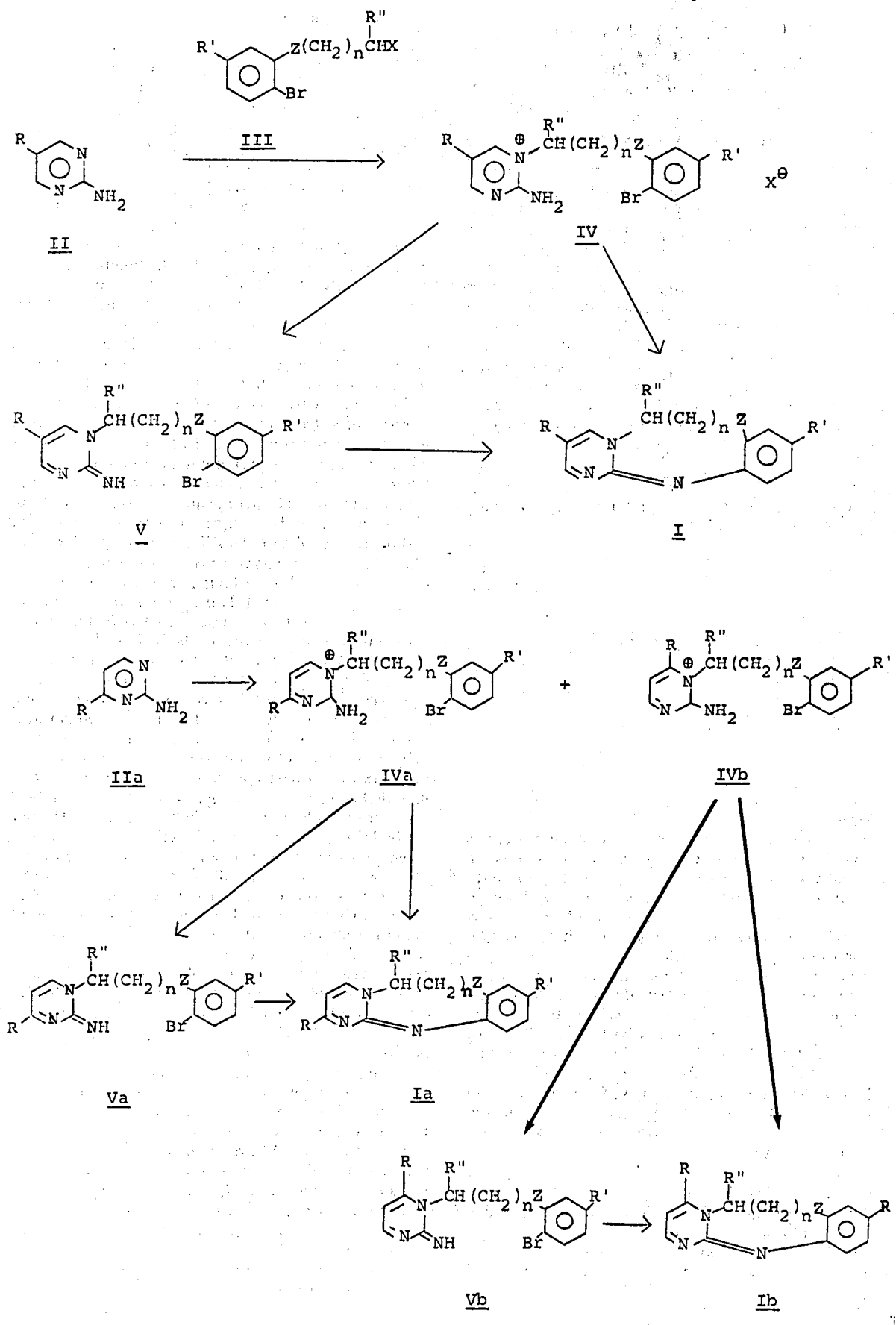

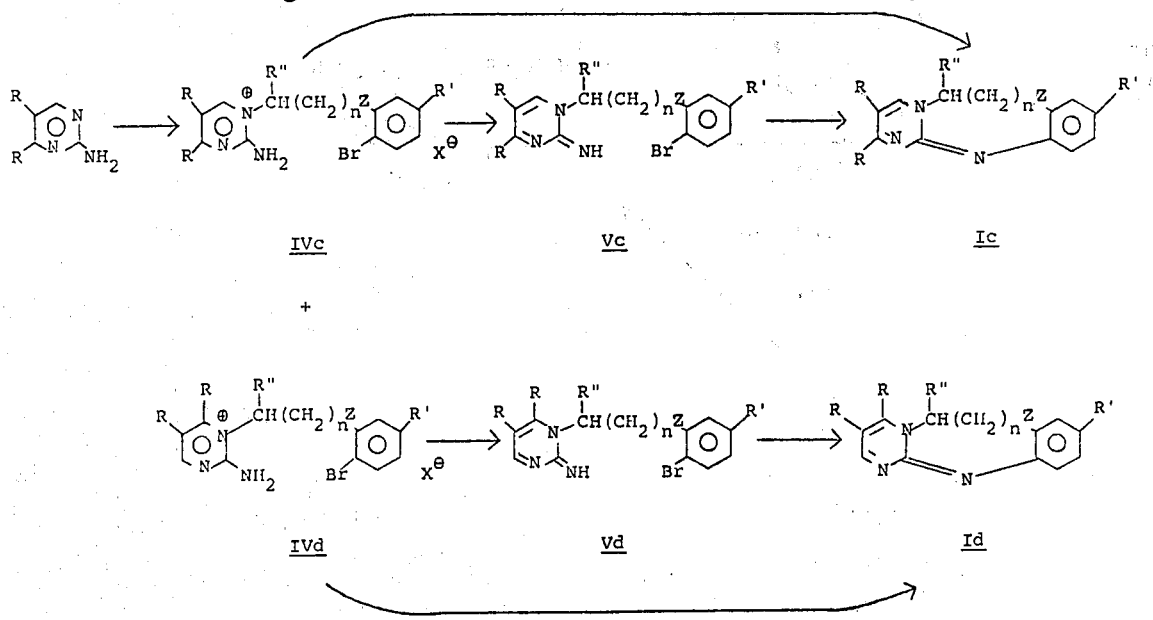

The intermediates of formula III wherein $n$ is O and Z is S may be prepared by refluxing about equimolar amounts of a 1,1-dibromoalkane or a 1-bromo-1-chloroalkane of 1 to 4 carbons VI with a saturated solution of $Na_2SO_3$ for a period of from about 40 to about 120 hours. The resulting 1-bromoalkane-1-sodium sulfonate VII is then reacted by heating with about equimolar amounts of an o-bromothiophenol VIII in the presence of aqueous alkali to yield a sodium o-bromophenylthioalkylene sulfonate IX. Treatment of the latter with $PCl_5$ or $PBr_5$ at ambient temperature yields the corresponding o-bromophenylthioalkyl chloride or bromide X. The foregoing reaction sequence is illustrated by the following equations

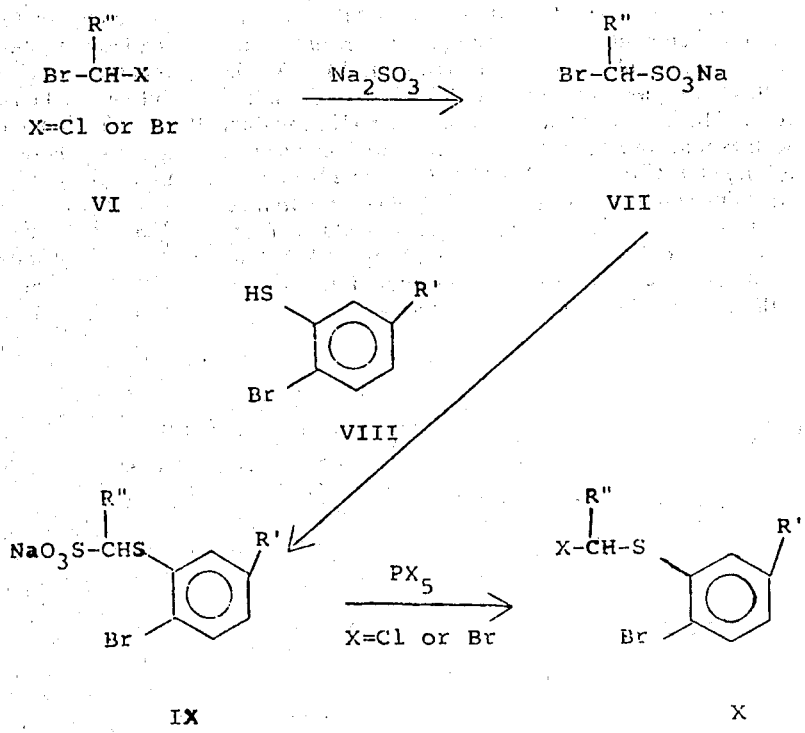

The intermediates of formula III wherein $n$ is 1 and Z is S may be prepared by reacting a 1-bromo-2-chloroalkane of formula XI with about equimolar amounts of a compound of formula VIII in the presence of aqueous alkali. Alternatively, a compound of formula XII may be prepared by reacting an o-bromophenylthioalkanol XIII with $PCl_5$ or $PBr_5$. The foregoing reaction sequence is illustrated by the following equations

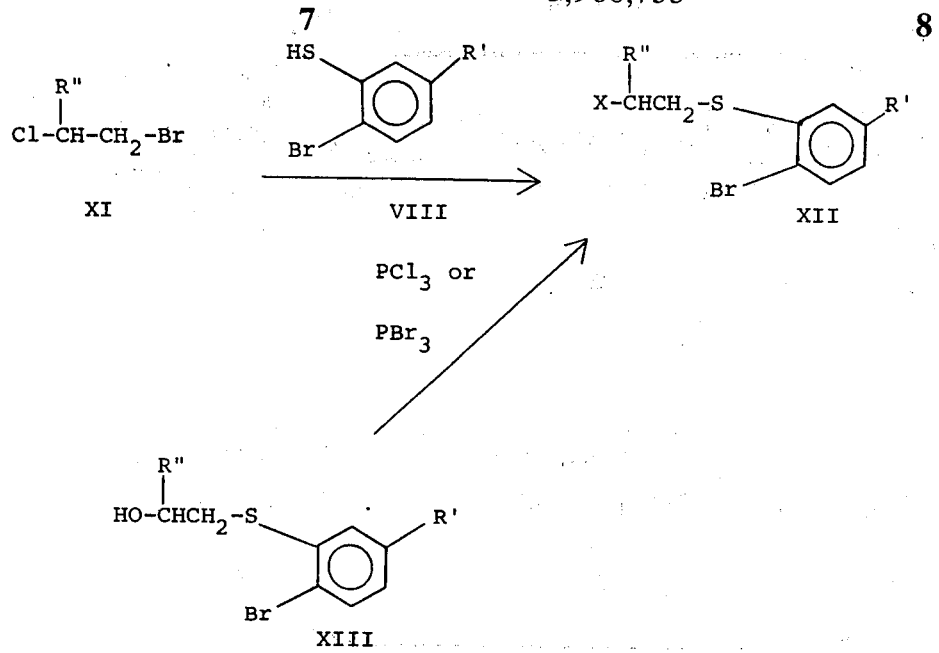

Compounds of formula VIII wherein R' is H, halogen, alkyl of from 1 to 4 carbons, phenyl, dialkylamidosulfonyl or trifluoromethyl may be prepared by reacting and R'-substituted aniline XXIV with N-bromosuccinimide in $CCl_4$ according to the procedure of Arcoria et al., Ann. Chim. (Rome), 54 139–155 (1964) to yield an o-bromo-R'-substituted aniline XXV. The latter is treated with $NaNO_2$ in HCl and then with $SO_2$ according to the procedure of Mecrwein et al., J. prakt. Chem. 152, 237 (1939) to yield the corresponding sulfonyl chloride XXVI. The latter is treated with Zn in $H_2SO_4$ according to the procedure of Organic Syntheses, Collective Volume I, pp. 504–506 to yield the desired o-bromo-R'-substituted thiophenol VIII. The reaction sequence is as follows:

Compounds of the formula III wherein Z is $SO_2$ may be prepared by converting a compound of formula XXV to the diazonium chloride XXVIII following the procedure of Meerwein, et al. supra, and converting the latter to the sulfonyl chloride XXIX following the procedure of Meerwein et al., supra. The sulfonyl chloride is then converted to the sodium sulfinate XXX by reduction with zinc following the procedure of Organic Syntheses, Coll. Vol. 1, pp. 492 (1941). Reacting the sodium sulfinate XXX with a 1,1-dihaloalkane following the procedure of Michael et al., J.A.C.S., 6, p. 253 (1884) gives the compound of formula III wherein Z is $SO_2$ and n is O. Reacting the sodium sulfinate XXX with a 1-bromo-2-chloroalkane following the procedure of Michael et al., supra, gives the compound of

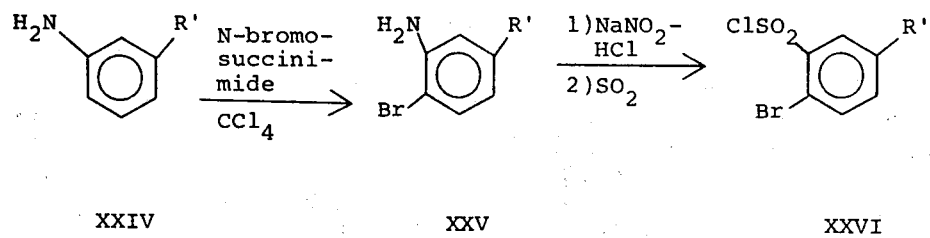

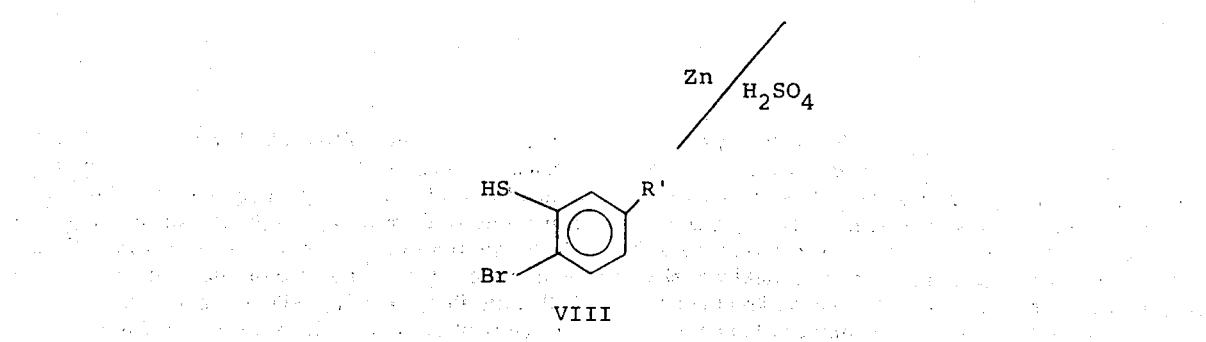

formula III wherein Z is SO₂ and n is 1. The foregoing reaction sequence is illustrated by the following equations:

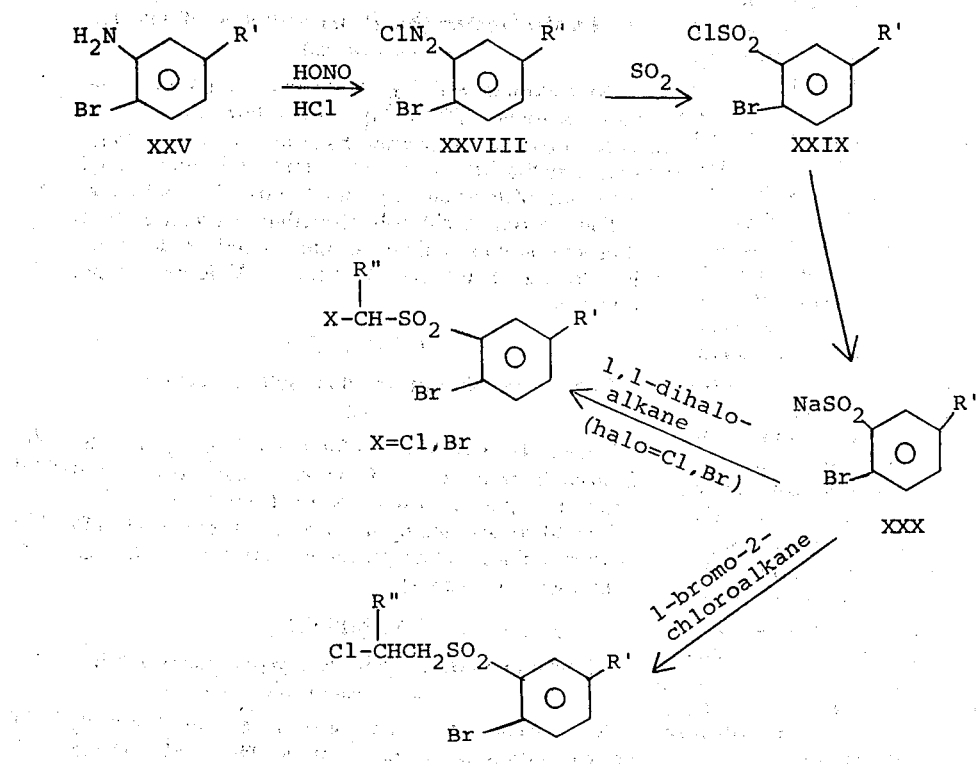

The compounds of the present invention may be administered to mammalian species as central nervous system stimulants and as muscle relaxants. In the rat, responses to the stimulant activity of the compounds of the present invention include increased activity and body tremors. The muscle relaxant properties manifest themselves by responses that include decreased limb tone, decreased grip strength, and limb paralysis. In both the stimulant and muscle relaxant activities, the onset of activity is rapid, i.e., within about 15 minutes; the activity persists for about 2 hours or longer. In the rat the dosage range varies from about 6.25 to about 50 mg/kg for both activities, while in humans the dosage range varies from about 40 to about 2000 mg. daily in about four divided doses for both activities.

In addition to serving as intermediates for the preparation of compounds of formula I, the pyrimidinium compounds of formula IV are themselves effective bactericides.

Microbial bioassays, as described in "The Microbial World," by R. Y. Stanier, M. Doudoroff and E. A. Adelberg, Prentice-Hall, Inc., Englewood Cliffs, N.J. 3rd Ed., p. 858, are employed to determine the bactericidal properties of the pyrimidinium compounds IV of this invention. The bacteria employed include *Staphylococcus aureus*, 1, *Streptococcus pyogenes*, 2, *Salmonella scho'tmuelleri*, 3, *Salmonella gallinarum*, 4, *Pseudomonas aeruginosa*, 5, *Proteus vulgaris*, 6, *Escherichia coli*, 7, *Pasturella multocida*, 8, and *Mycobacterium tuberculosis*, 9.

In the procedure, a sterile agar plate is seeded with the test organism, and then a number of glass cylinders are placed on its surface, forming a series of little cups. A known dilution of the compounds of this invention is added to each cup and the entire plate is then incubated until significant bacterial growth has occurred. The compounds of this invention diffuse out of the cup into the surrounding agar and produce a zone of inhibition. In this fashion it is possible to find the minimum inhibiting concentration (mic), of the compound that produces a recognizable zone of inhibition. The following summarizes the data.

| Micro-organism | mic of Pyrimidinium Compound, Micrograms, (mcg)/ml | | | |
|---|---|---|---|---|
| | Compound of Ex. 1 | Compound of Ex. 27 | Compound of Ex. 29 | Compound of Ex. 38 |
| 1 | 3.13 | 12.5 | 6.25 | 6.25 |
| 2 | 12.5 | 50.0 | 50.0 | 25.0 |
| 3 | 12.5 | 50.0 | 12.5 | 12.5 |
| 4 | 6.25 | 25.0 | 12.5 | 12.5 |
| 5 | 12.5 | 25.0 | 25.0 | 25.0 |
| 6 | 12.5 | 25.0 | 25.0 | 25.0 |
| 7 | 3.13 | 25.0 | 12.5 | 6.25 |
| 8 | 6.25 | 12.5 | 25.0 | 12.5 |
| 9 | 0.39 | 6.25 | 1.57 | 0.78 |

The compounds of the present invention in the described dosages may be administered orally; however, other routes such as intraperitoneally, subcutaneously, intramuscularly or intravenously may be employed.

The active compunds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of this invention include the pharmaceutically acceptable acid-additional salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic acid, theophylline, 8-chlorotheophylline, p-aminobenzoic, p-acetamidobenzoic, or methanesulfonic.

The following examples illustrate the invention without, however, limiting the same thereto. All temperatures given are in degrees Centigrade.

EXAMPLE 1

[(o: Bromophenyl)thio]methanesulfonic acid, sodium salt

To a solution of 40.0 g of o-bromobenzenethiol in aqueous sodium hydroxide (10.0 g of sodium hydroxide in 40 ml of water) is added 60.0 g of bromomethanesulfonic acid, sodium salt and the mixture is heated so that the water distills. To the dry residue is added a second portion of 40 ml of water and the distillation to dryness is repeated. The dry residue is heated for three hours, cooled, and dissolved in 600 ml of hot water. The pH is adjusted to 5.0 and cooled to give about 63.3 g of the named compound, mp>310°.

EXAMPLE 2 o-Bromophenyl chloromethyl sulfide

A mixture of 60.4 g of [o-bromophenyl)thio]methanesulfonic acid, sodium salt and 98.0 g of phosphorus pentachloride is blended until liquified, diluted with 600 ml of ether, and then poured on 1.2 kg of crushed ice. The ether layer is separated, washed, dried, and concentrated to give about 43.7 g of the named compound, bp about 86°(0.6 mm), mp about 28°–30°.

EXAMPLE 3

2-Amino-1-[[(o-bromophenyl)thio]methyl]-pyrimidinium chloride

To a solution of 14.1 g of 2-aminopyrimidine in 180 ml of xylene is added a solution of 24.0 g of o-bromophenyl chloromethyl sulfide in 40 ml of xylene. The mixture is heated at 90°–95° for about 15 hours to give about 27.3 g of the named compound.

EXAMPLE 4

[(2-Bromo-5-chlorophenyl)thio]methanesulfonic acid, sodium salt

To a solution of 49.2 g of 2-bromo-5-chlorobenzenethiol in 40 ml of 25% aqueous sodium hydroxide is added 60.0 g of bromomethanesulfonic acid, sodium salt, and the procedure of example 1 is reproduced. The yield of the named product, mp>310°, is 69.2 g.

The 2-bromo-5-chlorobenzenethiol is prepared from 2-bromo-5-chloroaniline via the procedure described in Organic Syntheses, Collective Volume 3, pp. 809–811.

EXAMPLE 5

[(2-Bromo-5-tolyl)thio]methanesulfonic acid, sodium salt

When 44.7 g of 2-bromo-5-toluenethiol replaces the 2-bromobenzenethiol in Example 1, there is obtained about 65.7 g of the named product, mp>300°.

The 2-bromo-5-methyl-toluenethiol is prepared from 2-bromoaniline by the procedure reported in Organic Syntheses (vide supra).

EXAMPLE 6

[(2-Bromo-5-($\alpha,\alpha,\alpha$-trifluorotolyl]methanesulfonic acid, sodium salt A. to 161.0 g of m-aminobenzotrifluoride and 10.0 g of iron filings is added, dropwise, with agitation at 35°–40°, 160.0 g of bromine, using a slow stream of nitrogen to sweep out the evolved hydrogen bromide. Subsequently, the mixture is agitated for an additional 2 hours and then distilled in vacuo to give 4-bromo-3-aminobenzotrifluoride.

B. The product from (A) is subjected to the procedure of Organic Syntheses (vide supra) to give 2-bromo-5-$\alpha,\alpha$, $\alpha$-trifluorotoluenethiol.

c. By substituting 56.6 g of 2-bromo-5-$\alpha,\alpha,\alpha$-trifluoro-toluenethiol for the o-bromobenzenethiol in example 1, there is obtained about 70.2 g of 2-bromo-5-($\alpha,\alpha,\alpha$-trifluorotoyl)thio]methanesulfonic acid, sodium salt, mp>300°.

EXAMPLE 7

6H-Pyrimido[1,2-c][1,3,5]benzothiadiazepine

A mixture of 33.2 g of 2-amino-1-[[(o-bromophenyl)-thio]methyl]pyrimidinium chloride, 27.7 g of anhydrous potassium carbonate, 0.8 g of copper bronze, and 750 ml of n-propanol is heated and stirred, under reflux, for 6 days, filtered hot, and the filtrate concentrated to dryness in vacuo. The residue is dissolved in 600 ml of ether, and the ether solution is washed, dried, decolorized with Darco, and concentrated to give about 23.7 g of a yellow solid. Recrystallization from cyclohexane-benzene gives about 17.4 g of the named compound.

EXAMPLE 8–12

By employing the procedure described in Organic Syntheses, Collective Volume 3, pp. 809-811, the aniline derivatives in Column 1 are converted to the thio derivatives in Column 2, and the latter derivatives following the procedure of examples 1 and 2, give the chloromethyl sulfides in Column 3.

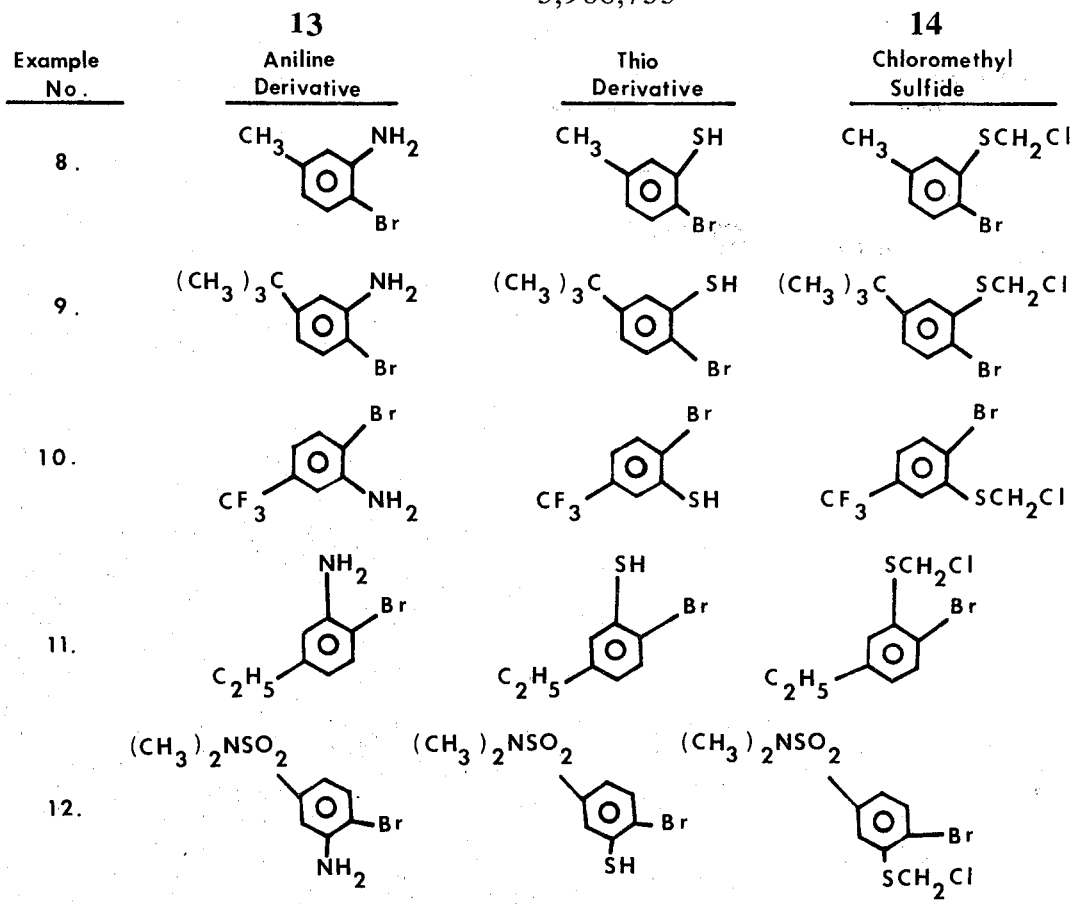

EXAMPLES 13-21

By substituting an equivalent amount of the chloromethyl sulfides of Column 3, examples 8-12, for the o-bromophenyl chloromethyl sulfide in example 3, and an equivalent amount of the substituted aminopyrimidine in Column 2 for the aminopyrimidine in example 3 and employing the procedure of that example, the pyrimidinium chlorides shown in Column 3 are obtained.

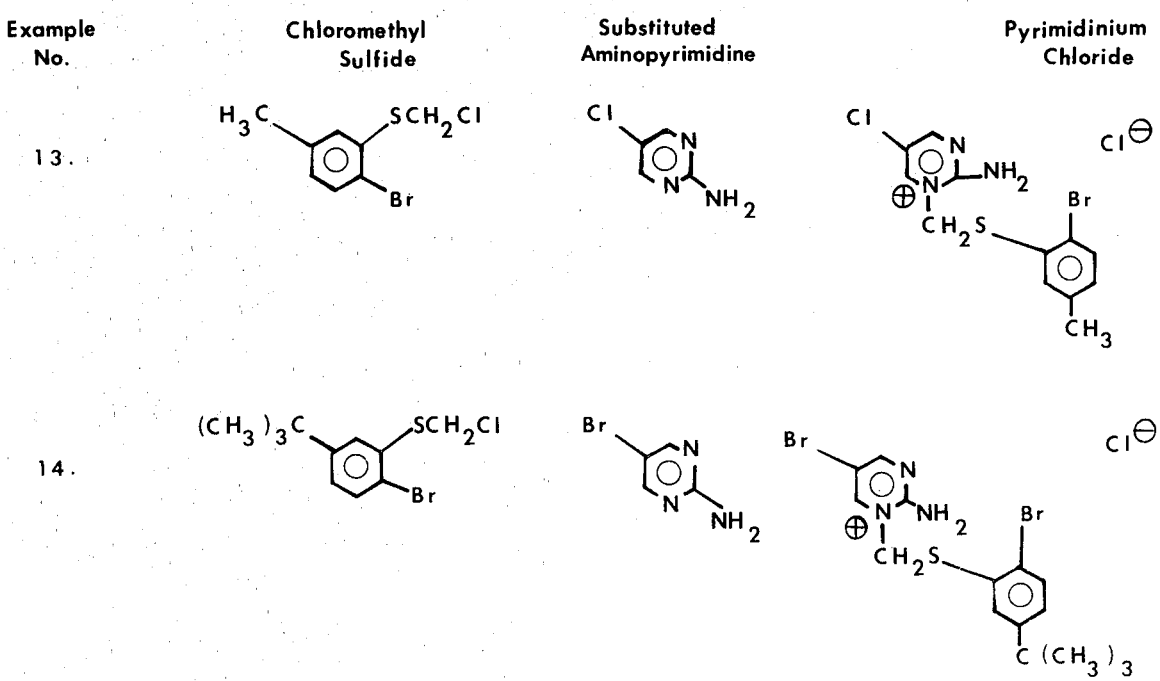

| Example No. | Chloromethyl Sulfide | Substituted Aminopyrimidine | Pyrimidinium Chloride |
|---|---|---|---|
| 15. | 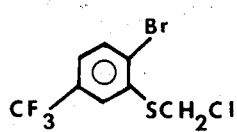 | 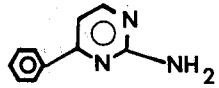 | 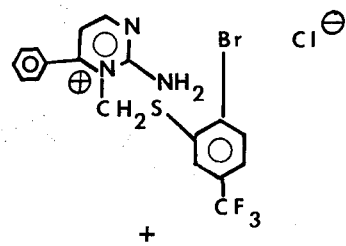 + |
| 16. | 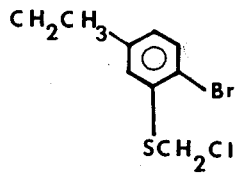 | 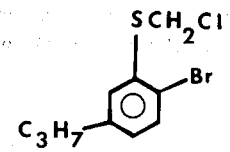 | 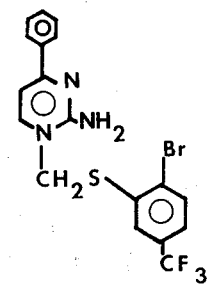 |
| 17. | 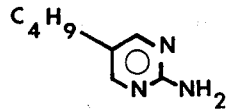 | 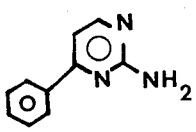 | 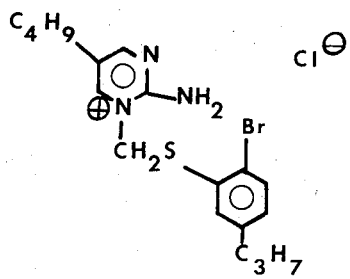 |
| 18. | 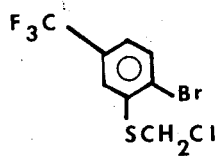 | 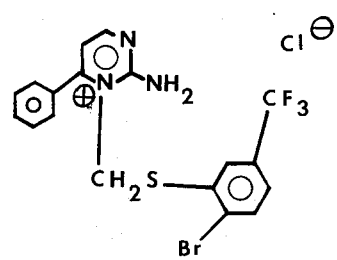 | 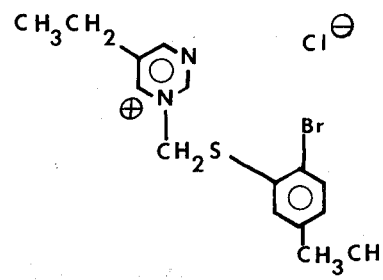 + 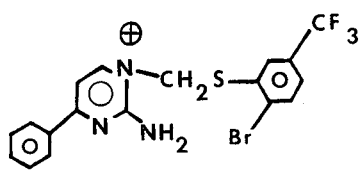 |

-continued
| Example No. | Chloromethyl Sulfide | Substituted Aminopyrimidine | Pyrimidinium Chloride |
|---|---|---|---|
| 19. | 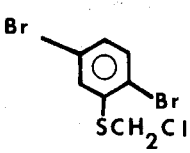 | 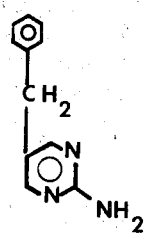 | 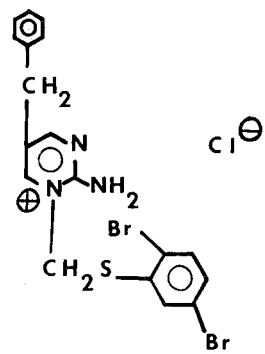 |
| 20. | 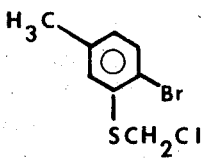 | 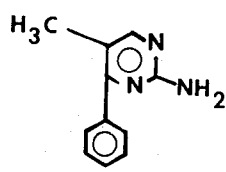 | 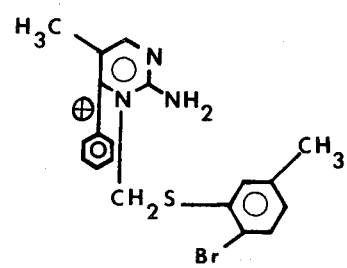 + 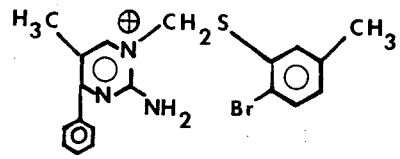 |
| 21. | 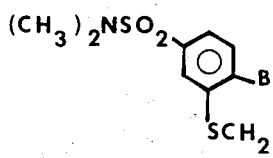 | 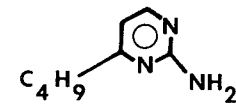 | 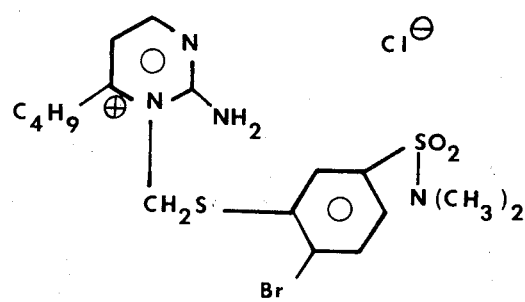 + 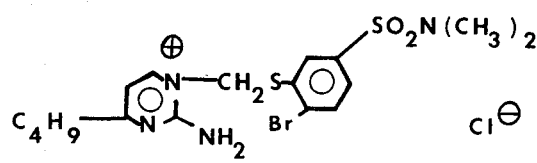 |

EXAMPLE 22

[(2-Bromo-5-chlorophenyl)thio]methanesulfonic acid, sodium salt

By substituting 49.2 g of 2-bromo-5-chlorobenzenethiol for the 2-bromo-4-chlorobenzenethiol in example 4, there is obtained 68.7 g of the named product, mp>300°.

EXAMPLE 23

2-Imino-1-[[(o-bromophenyl)thio]methyl]pyrimidine

To a suspension of 13.8 g of anhydrous potassium carbonate in 150 ml of anhydrous n-propanol is added 33.1 g of 2-amino-1-[[(o-bromophenyl)thio]methyl]-pyrimidinium chloride, portionwise, under nitrogen, at room temperature, with stirring. Subsequently, the mixture is stirred and heated under reflux for 2 hours, filtered hot, and the filtrate concentrated in vacuo. The residue is partitioned between 200 ml each of water and ether, the ether layer is separated, dried, and concentrated to give about 28.7 g of the named compound, after recrystallization from pentane.

EXAMPLE 24

6H-Pyrimido[1,2-c][1,3,5]benzthiadiazepine Hydrochloride .$H_2O$

A mixture of 14.8 g of 2-imino-1-[[(o-bromophenyl)-thio]methyl]pyrimidine, 13.8 g of anhydrous potassium carbonate, 0.5 g of copper bronze, and 400 ml of anhydrous n-propanol is stirred and heated under nitrogen for about 80 hours, filtered hot, and the filtrate concentrated to dryness in vacuo. The residue is distributed between 250 ml of water and ether, the ether layer is separated, dried, and concentrated to give about 7.2 g of the base product. By the usual methods, the base gives a hydrochloride, monohydrate.

EXAMPLE 25

2-Bromo-5-chlorophenyl chloromethyl sulfide

A mixture of 68.2 g of the product from example 4 and 98.0 g of phosphorus pentachloride is blended until liquefaction occurs, diluted with 600 ml of ether and then poured on 1.3 kg of crushed ice. Workup of the ether layer yields about 47.3 g of the named compound, bp about 98° (0.5 mm.).

EXAMPLE 26

2-Amino-1-[[(2-bromo-5-chlorophenyl)thio]methyl]-pyrimidinium chloride

To a solution of 18.8 g of 2-aminopyrimidine in 180 ml of benzene is added 54.6 g of the product from example 25, and the mixture stirred and heated under reflux for about 12 hours. The cooled mixture is filtered to give about 62.8 g of the named compound, mp about 240°–242°.

EXAMPLE 27

3-Chloro-6H-pyrimido[1,2-c][1,3,5]benzothiadiazepine Hydrochloride $H_2O$

A mixture of 7.4 g of the product from example 26, 2.8 g of anhydrous potassium carbonate, 0.1 g of copper bronze, and 100 ml of anhydrous n-butanol is heated at 110° for about 15 hours. Workup as in example 7 yields about 3.6 g of the named compound.

EXAMPLES 28–41

By substituting equivalent amounts of the pyrimidinium chlorides in column 2 for the 2-amino-1-[[(o-bromophenyl)-thio]methyl]pyrimidinium chloride in example 7, the correspondingly substituted 6H-pyrimido[1,2-c][1,3,5]benzothiadiazepines shown in column 3 are obtained.

| Example No. | Pyrimidinium Chloride | Substd. 6H-pyrimido [1,2-c][1,3,5]-benzothiadiazepines |
|---|---|---|
| 28. | 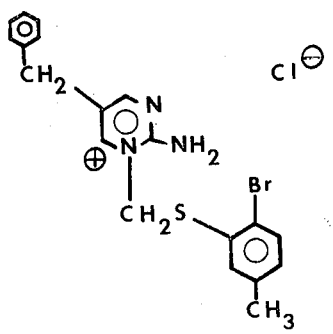 | 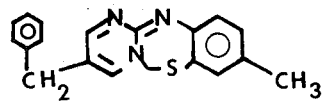 |
| 29. | 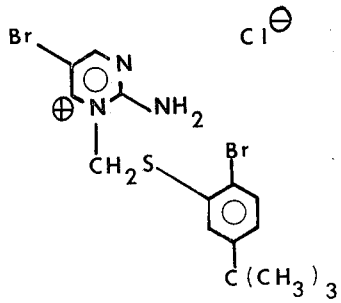 | 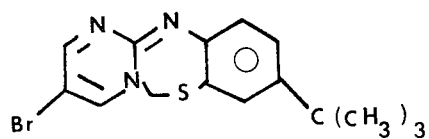 |

-continued
| Example No. | Pyrimidinium Chloride | Substd. 6H-pyrimido [1,2-c][1,3,5]-benzothiadiazepines |
|---|---|---|
| 30. | 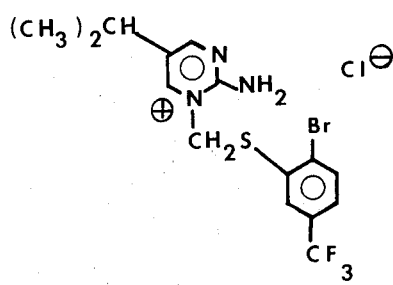 | 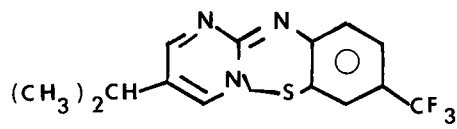 |
| 31. | 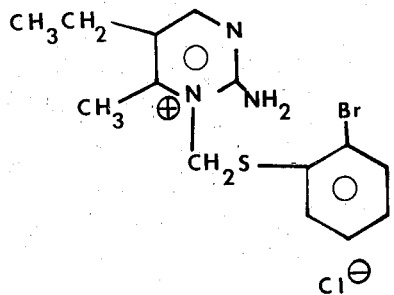 | 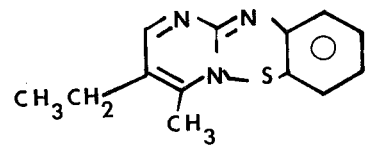 |
| 32. | 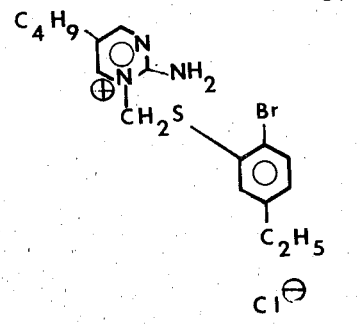 | 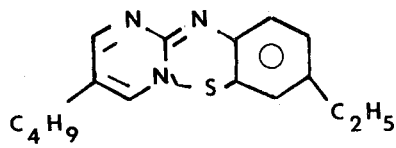 |
| 33. | 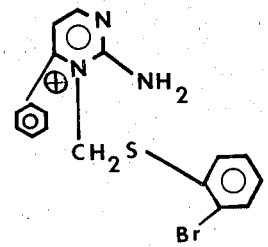 | 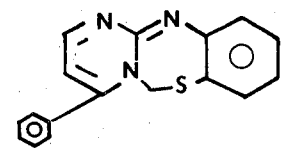 |
| 34. | 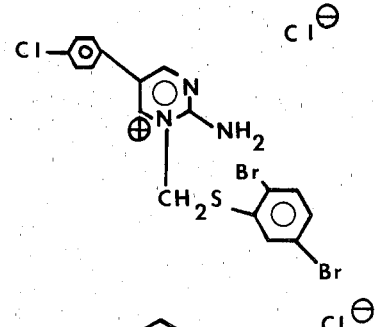 | 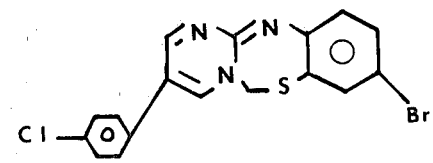 |
| 35. | 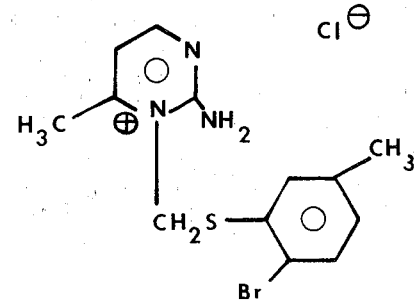 | 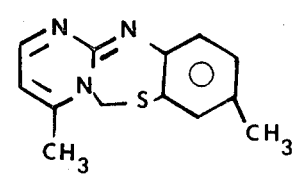 |

| Example No. | Pyrimidinium Chloride | Substd. 6H-pyrimido [1,2-c][1,3,5]-benzothiadiazepines |
|---|---|---|
| 36. | C₄H₉ pyrimidinium Cl⁻ with CH₂S, SO₂N(CH₃)₂, Br substituents | C₄H₉ substituted 6H-pyrimido[1,2-c][1,3,5]benzothiadiazepine with SO₂N(CH₃)₂ |

EXAMPLE 37

6H-Pyrimido[1,2-c][1,3,5]benzothiadiazepine, hydrochloride

To a solution of 1.0 g of 6H-pyrimido[1,2-c][1,3,5]-benzothiazdiazepine in 20 ml of anhydrous 2-propanol is added about 5.0 ml of 4.2 N 2-propanolic hydrogen chloride. The clear solution that is formed is diluted with anhydrous ether until a turbidity persists and is then cooled to give the pale yellow crystalline product. Recrystallization from acetonitrile gives about 1.0 g of the named product.

EXAMPLE 38

6,7-Dihydro-7-n-propylpyrimido[1,2-d][1,4,6]benzothiadiazocine, hydrochloride A. o-Bromophenyl 2-chloro-1-pentyl sulfide To a solution of 23.0 g of sodium metal is 500 ml of absolute ethanol is added, in about 0.5 hour, a solution of 173.0 g of o-bromothiophenol in 250 ml of absolute ethanol. The mixture is stirred and heated under reflux for about 0.5 hour, cooled to 0°, and treated, dropwise, with 185.5 g of 1-bromo-2-chloropentane. The addition requires about 1 hour. The mixture is stirred for about 2 hours at 0°, warmed slowly to reflux, and then heated under reflux for 2 hours. The mixture is filtered and the filtrate concentrated in vacuo at 40° to give about 255.7 g of o-bromophenyl 2-chloro-1-pentyl sulfide as a pale yellow oil.

B. 2-Amino-1-[2'-(o-bromophenylthio-1-pentyl)]-pyrimidinium chloride

To a solution of 58.7 g of the product from A and 18.4 g of 2-aminopyrimidine in 200 ml of anhydrous toluene is heated under reflux for about 6 hours, cooled, and the crystalline product filtered to give about 67.2 g of the title compound as a pale yellow crystalline solid.

C. 1-[2'-(o-Bromophenylthio-1-penty)]-1,2-dihydro-2-iminopyrimidine

To a solution of 7.7 g of the product from B in 100 ml of 95% ethanol is added 2.8 g of potassium carbonate and the mixture is stirred at about 40° for 1 hour, filtered and the filtrate concentrated in vacuo. The residue is recrystallized from cyclohexane to give 6.3 g of 1-[2'-(o-bromophenylthio)-1-pentyl)]-1,2-dihydro-2-iminopyrimidine as a pale yellow crystalline solid.

D. 6,7-Dihydro-7-n-propylpyrimido[1,2-d][1,4,6]-benzothiadiazocine, hydrochloride The product from C, 15.4 g, 13.8 g of anhydrous micronized potassium carbonate, 0.5 g of copper bronze and 100 ml of anhydrous n-butanol are stirred and heated under reflux for about 6 days, filtered, and the filtrate concentrated, in vacuo, to give the product as a deep yellow-colored viscous oil. The oil, 12.7 g, in 120 ml of anhydrous ether, is cooled to 0° and treated slowly, with stirring with 10 ml of 1.5 N ethereal hydrogen chloride. The solid that separates is filtered, and recrystallized from 2-propanol to give the title compound, as a pale yellow crystalline product.

EXAMPLES 39–41

Following the procedure of examples 1–7 but substituting for bromomethanesulfonic acid, sodium salt in example 1 the bromoalkylsulfonic acid, sodium salt listed in column I, there is obtained the compound of formula I

[Structure with R" group: pyrimidine-N-CH(R")-S-phenyl fused ring system]

wherein R" is the radical indicated in column II.

| | I | II |
|---|---|---|
| 39. | 1-bromoethane-1-sulfonic acid, sodium salt | —CH₃ |
| 40. | 1-bromobutane-1-sulfonic acid, sodium salt | —CH₂CH₂CH₃ |
| 41. | 1-bromo-2-methylpropane-1-sulfonic acid, sodium salt | —CH(CH₃)₂ |

EXAMPLE 42

3-Trifluoromethyl-6H-pyrimido[1,2-c][1,3,5]benzothiadiazepine-5,5-dioxide

A. α,α,α-Trifluoro-m-acetoluidide

To a solution of 161.0 g of α, α, α-trifluoro-m-toluidine in 500 ml of 2N hydrochloric acid, at room temperature, with vigorous agitation, is added rapidly 102.0 g of acetic anhydride. An exothermic reaction occurs and the temperature is allowed to rise spontaneously to about 50°. Subsequently, the mixture is allowed to cool to room temperature, and then cooled in ice. The crystalline solid is filtered to give 189.3 g of α,α,α-trifluoro-m-acetotoluidide.

B. α,α,α-Trifluoro-m-N,N-diacetotoluidide

The product from A, 102.0 g, and 500 ml of acetic anhydride are heated under reflux for about 18 hours. The mixture is then concentrated in vacuo to remove the excess of acetic anhydride. The residual solid crystallizes and is recrystallized from heptane to give 136.7 g of α,α,α-trifluoro-m-N,N-diacetotoluidide.

C. 2-Bromo-α,α,α-trifluoro-m,N,N-diacetotoluidide

To a solution of 50.6 g of the product from B in 120 ml of carbon tetrachloride is added 35.6 g of N-bromosuccinimide and the mixture is stirred and heated under reflux for about 0.25 hours. Workup according to the procedure of Arcoria and Scarlata [*Ann. Chim.* (Rome), 54, 139 (1964)] yields about 58.7 g of 2-bromo-α,α, α-trifluoro-m-N,N-diacetotoluidide.

D. 2-Bromo-α,α,α-trifluoro-m-toluidine Hydrochloride

The product from C, 58.0 g, 250 ml of 95% ethanol, and 10.0 ml of concentrated hydrochloric acid are heated under reflux for about 1 hour and then concentrated to dryness in vacuo. The residue crystallizes on cooling to give about 45.3 g of 2-bromo-α,α,α-trifluoro-m-toluidine hydrochloride.

E. 2-Bromo-α,α,α-trifluoro-m-toluenesulfonyl chloride

Following the procedure of Merrwein, et al, *J. prakt. Chem.*, 152, 237 (1939), 27.8 g of the product from D in 100 ml of 25% hydrochloric acid, at 0°, is treated dropwise, with a solution of 6.9 g of sodium nitrite in 14 ml of water. Subsequent to the addition, the mixture is stirred at 0° for 0.5 hour, 0.5 g of cupric chloride is added and while kept at 0°, a rapid stream of sulfur dioxide is introduced into the reaction mixture for 0.5 hour. Subsequently, the mixture is slowly warmed to 50° while the introduction of sulfur dioxide continues. Workup of the reaction mixture gives 25.6 g of 2-bromo-α,α,α-trifluoro-m-toluenesulfonyl chloride.

F. Sodium 2-bromo-α,α,α-trifluoro-m-toluenesulfonate

Into a suspension of 15.6 g of zinc dust in 115 ml of water is introduced dry steam until the internal temperature reaches 70°. The steam is shut off, and 32.4 g of the product from E is added in small portions during about 10 minutes. Stirring is maintained throughout the addition and for about 10 minutes afterwards. Steam is again introduced into the mixture, with stirring, until the internal temperature reaches 90° at which time the steam is shut off and 10 ml of 12N aqueous sodium hydroxide is added followed by 2.0 g portions of solid sodium carbonate until the mixture is strongly alkaline. Following this, the procedure of *Org. Syntheses, Coll. Vol* 1, 492 (1941) is followed to give about 24.7 g of sodium 2-bromo-α,α,60 -trifluoro-m-toluenesulfonate.

G. 2-Bromo-α,α,α-trifluoro-m-tolyl Bromomethyl Sulfone

A mixture of 31.1 g of the product from F, 34.8 g of 1,1-dibromoethane, 500 ml of absolute ethanol, 13.8 g of anhydrous, micronized potassium carbonate, and 0.5 g of copper bronze is stirred and heated under reflux for about 9.5 hours. The hot solution is filtered and the filtrate concentrated to a volume of about 100 ml and cooled. The product that crystallizes is filtered to give about 30.6 g of 2- bromo-α,α,α-trifluoro-m-tolyl bromomethyl sulfone.

H. 3-Trifluoromethyl-6H-pyrimido[1,2-c][1,3,5]benzothiadiazepine-5,5-dioxide

Following the procedure of example 3 but substituting for o-bromophenyl chloromethyl sulfide an equivalent amount of the product from part G, there is obtained 2-amino-1-[[2-bromo-5-α,α,α-trifluoro-m-tolyl)sulfonyl]methyl]pyrimidinium bromide. Following the procedure of example 7 but substituting the above pyrimidinium bromide from 2-amino-1-[[o-bromophenyl)-thio[methyl]pyrimidinium chloride, the title compound is obtained.

EXAMPLES 43–46

Following the procedure of example 42 but substituting for 1,1-dibromomethane in part G the dihaloalkane listed below in column I, there is obtained the compound of formula I of the formula $$\text{(pyrimido-benzo structure with substituent } -\text{CH}(\text{CH}_2)_n\text{SO}_2-\text{C}_6\text{H}_3-\text{CF}_3 \text{ and } R'')$$

wherein R" and n are as indicated in columns II and III:

| | I | II | III |
|---|---|---|---|
| 43. | 1-bromo-2-chloroethane | H | 1 |
| 44. | 1,1-dibromoethane | —CH$_3$ | 0 |
| 45. | 1,1-dibromo-2-metylpropane | —CH(CH$_3$)$_2$ | 0 |
| 46. | 1-bromo-2-chloropentane | —C$_3$H$_7$ | 1 |

EXAMPLE 47

Preparation of capsule formulation

| Ingredient | Milligrams per Capsule |
|---|---|
| 6H-Pyrimido[1,2-c][1,3,5]benzothiadiazepine, hydrochloride | 400 |
| Starch | 80 |
| Magnesium stearate | 5 |

The active ingredient, starch and magnesium stearate are blended together. The mixture is used to fill hard shell capsules of a suitable size at a fill weight of 485 milligrams per capsule.

EXAMPLE 48

Preparation of tablet formulation

| Ingredient | Milligrams per Tablet |
|---|---|
| 6H-Pyrimido[1,2-c][1,3,5]benzothiadiazepine-5,5-dioxide | 300 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The web granules are passed through a No. 8 screen and dried at 120°F. The dry granules are passed through a No. 16 screen. The mixture is lubricated with magnesium stearate and compressed into tablets in a suitable tableting machine. Each tablet contains 300 milligrams of active ingredient.

EXAMPLE 49

Preparation of oral syrup formulation

| Ingredient | Amount |
|---|---|
| 6,7-Dihydro-7-n-propylpyrimido-[1,2-d]-[1,4,6]benzothiadiazocine, hydrochloride | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & Co. No. 2) | 10 mg. |
| Cherry flavor | 50 mg. |
| Distilled water qs to | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of the formula

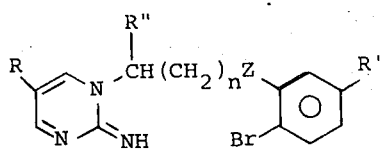

wherein
R is hydrogen,
R' is hydrogen, F, Cl, Br, CF$_3$, alkyl of from 1 to 4 carbons, or dialkylamidosulfonyl wherein each alkyl radical has from 1 to 4 carbons;
n is 0 or 1;
R" is hydrogen or alkyl of from 1 to 4 carbons; and
Z is S or SO$_2$.

2. A compound as defined in claim 1 wherein Z is S, and R' is hydrogen.

3. A compound as defined in claim 2 wherein R" is hydrogen.

4. A compound as defined in claim 2 wherein R" is alkyl of from 1 to 4 carbons.

5. A compound of claim 1 which is 2-imino-1-[[(o-bromophenyl)thio]methyl]pyrimidine.

6. A compound of claim 1 which is 1[2'-(o-bromophenylthio-1-pentyl)]-1,2-dihydro-2-iminopyrmidine.

7. A compound of the formula

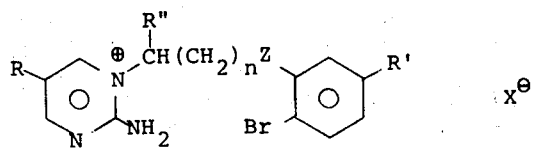

wherein
R is hydrogen,
R' is hydrogen, F, Cl, Br, CF$_3$, alkyl of from 1 to 4 carbons, or dialkylamidosulfonyl wherein each alkyl radical has from 1 to 4 carbons;
n is 0 or 1;
R" is hydrogen or alkyl of from 1 to 4 carbons; and
Z is S or SO$_2$, and
X is Br or Cl.

8. A compound as defined in claim 7 wherein R' is hydrogen or Cl, and Z is S.

9. A compound as defined in claim 8 wherein R" is hydrogen.

10. A compound as defined in claim 8 wherein R" is alkyl of 1 to 4 carbons.

11. A compound of claim 7 which is 2-amino-1[[(2-bromo-4-chlorophenyl)thio]methyl]pyrimidinium chloride.

12. A compound of claim 7 which is 2-amino-[2'-(o-bromophenylthio-1-pentyl)]pyrimidinium chloride.

* * * * *

UNITED STATES PATENT AND TRADEMARK OFFICE
CERTIFICATE OF CORRECTION

PATENT NO. : 3,966,733
DATED : June 29, 1976
INVENTOR(S) : Harry Louis Yale et al It is certified that error appears in the above-identified patent and that said Letters Patent are hereby corrected as shown below:

Column 1, line 20, "composition" should read --compositions--.
Column 2, line 59, "va" should read --Va--.
Column 7, line 31, "and" should read --an--.
Column 7, line 36, "Mecrwein" should read --Meerwein--.
Column 11, line 25, "acid-additional" should read
  --acid-addition--.
Column 11, line 39, "o:" should read --o- --.
Column 11, line 55, "[o-" should read --[(o- --.
Column 12, line 30, after "trifluorotolyl" insert --)thio--.
Column 20, line 5, "example 4" should read --example 5--.
Column 25, line 21, "Merrwein" should read --Meerwein--.
Column 25, line 48, "α,α,60" should read --α,α,α--.
Column 25, line 69, "thio[" should read --thio]--.
Column 26, line 54" "web" should read --wet--.
Column 28, line 5, "1[2' " should read 1-[2'--.
Column 28, line 32, "1[[(2-" should read --1-[[(2- --.
Column 28, line 35, "2-amino-[2'-(o-" should read
  --2-amino-1-[2'-(o- --.

Signed and Sealed this

Twenty-sixth Day of October 1976

[SEAL]

Attest:

RUTH C. MASON
Attesting Officer

C. MARSHALL DANN
Commissioner of Patents and Trademarks